US012112846B2

(12) United States Patent
Hacker et al.

(10) Patent No.: US 12,112,846 B2
(45) Date of Patent: Oct. 8, 2024

(54) ELECTRONIC LABORATORY METERING SYSTEM FOR LIQUIDS AND METHOD FOR OPERATING AN ELECTRONIC LABORATORY METERING SYSTEM FOR LIQUIDS

(71) Applicant: Eppendorf AG, Hamburg (DE)

(72) Inventors: Jan-Hendrik Hacker, Hamburg (DE); Peter Molitor, Hamburg (DE)

(73) Assignee: Eppendorf SE, Hamburg (DE)

( * ) Notice: Subject to any disclaimer, the term of this patent is extended or adjusted under 35 U.S.C. 154(b) by 877 days.

(21) Appl. No.: 16/981,011

(22) PCT Filed: Mar. 12, 2019

(86) PCT No.: PCT/EP2019/056181
§ 371 (c)(1),
(2) Date: Sep. 15, 2020

(87) PCT Pub. No.: WO2019/175189
PCT Pub. Date: Sep. 19, 2019

(65) Prior Publication Data
US 2021/0110917 A1    Apr. 15, 2021

(30) Foreign Application Priority Data

Mar. 16, 2018   (EP) .................................... 18162322
Mar. 22, 2018   (EP) .................................... 18163436

(51) Int. Cl.
*G16H 40/67*        (2018.01)
*B01L 3/02*         (2006.01)
(Continued)

(52) U.S. Cl.
CPC ............ *G16H 40/20* (2018.01); *B01L 3/0293* (2013.01); *B01L 9/54* (2013.01); *G01N 35/1016* (2013.01);
(Continued)

(58) Field of Classification Search
CPC ........ G16H 40/20; G16H 10/40; G16H 40/40; G16H 40/67; G16H 70/20; B01L 3/0293;
(Continued)

(56) References Cited

U.S. PATENT DOCUMENTS 7,770,475 B2    8/2010   Magnussen et al.
2004/0089051 A1 5/2004   Camenisch
(Continued)

FOREIGN PATENT DOCUMENTS

EP    1452849 A1    9/2004
EP    3141909 A1    3/2017
(Continued)

OTHER PUBLICATIONS

International search report for patent application No. PCT/EP2019/056181 dated May 6, 2019.
(Continued)

*Primary Examiner* — Robert R Raevis
(74) *Attorney, Agent, or Firm* — Bachman & LaPointe, P.C.

(57) ABSTRACT

An electronic laboratory metering system for liquids includes an electrical hand-held metering device (2) having at least one operation sensor unit (5) that detects operation of the hand-held metering device (2) and generates operating data and stores same in a storage apparatus (6), wherein the hand-held metering device (2) has an interface module (7) for connecting the hand-held metering device (2) to an external network access apparatus (4) for transferring the operating data; the metering system (1), specifically a data processing system (3), has a comparison unit (9) to compare operating data with target operating data and/or to compare context parameter data from the context parameter sensor unit (8) with target context parameter data and to generate a comparison result. The metering system (1) includes a
(Continued)

documentation unit (10) designed to generate and store log data records including at least the operating data and/or the context parameter data. The documentation unit (10) is connected to the comparison unit (9) to transmit the comparison results from the comparison unit (9) to the documentation unit (10) and the documentation unit (10) stores the comparison results as part of the log data records to be assigned to the relevant operating data and/or context parameter data, to add to same after operation of the hand-held metering device (2) has ended.

11 Claims, 2 Drawing Sheets

(51) Int. Cl.
    *B01L 9/00*    (2006.01)
    *G01N 35/10*    (2006.01)
    *G16H 10/40*    (2018.01)
    *G16H 40/20*    (2018.01)
    *G16H 40/40*    (2018.01)
    *G16H 70/20*    (2018.01)

(52) U.S. Cl.
    CPC ............ *G16H 10/40* (2018.01); *G16H 40/40* (2018.01); *G16H 40/67* (2018.01); *G16H 70/20* (2018.01); *B01L 2200/143* (2013.01); *B01L 2300/023* (2013.01); *G01N 2035/1025* (2013.01)

(58) Field of Classification Search
    CPC ................ B01L 9/54; B01L 2200/143; B01L 2300/023; B01L 2300/022; B01L 3/0237; G01N 35/1016; G01N 2035/1025; G05B 15/00
    USPC .... 73/1.02, 64.56, 864.21, 864–864.25, 863, 73/863.01; 436/180; 422/501–526
See application file for complete search history.

(56) References Cited

U.S. PATENT DOCUMENTS

| | | | |
|---|---|---|---|
| 2004/0171171 A1* | 9/2004 | Appoldt | G01G 17/04 |
| | | | 422/534 |
| 2007/0056351 A1 | 3/2007 | Curtis et al. | |
| 2008/0031774 A1 | 2/2008 | Magnant et al. | |
| 2009/0288470 A1 | 11/2009 | Bentz et al. | |
| 2010/0226825 A1 | 9/2010 | Beckey et al. | |
| 2015/0182961 A1 | 7/2015 | Arnold et al. | |
| 2016/0279630 A1 | 9/2016 | Fracchia et al. | |
| 2021/0110917 A1 | 4/2021 | Hacker et al. | |

FOREIGN PATENT DOCUMENTS

| | | |
|---|---|---|
| EP | 3189896 A1 | 7/2017 |
| JP | 2004279414 A | 10/2004 |
| JP | 2013543438 A | 12/2013 |
| JP | 2015501218 A | 1/2015 |
| WO | 2012045415 A1 | 4/2012 |

OTHER PUBLICATIONS

Piston-operated volumetric apparatus—Part 2: Piston pipettes, ISO 8655-2:2002(E), Sep. 15, 2002.
Wireless network, Wikipedia, Mar. 8, 2018.
Andrew, Le Systeme de Pipetage Automatise, Andrew Alliance S.A., Apr. 9, 2014, Geneva, Switzerland, http://www.andrewalliance.com/.
I. Semac et al., Pipetting Performances By Means of the Andrew Robot, Andrew Alliance, 2013, Geneva, Switzerland, http://www.andrewalliance.com/.

* cited by examiner

ELECTRONIC LABORATORY METERING SYSTEM FOR LIQUIDS AND METHOD FOR OPERATING AN ELECTRONIC LABORATORY METERING SYSTEM FOR LIQUIDS

BACKGROUND OF THE INVENTION

The present invention relates to an electronic laboratory metering system for liquids, the metering system comprising at least one electrical handheld metering device having at least one operation sensor unit detecting the operation of the handheld metering device and generating corresponding operating data and, in particular, storing said operating data in a storage device of the handheld metering device, the handheld metering device having an interface module by means of which the handheld metering device can be connected to an external network access device via a data connection, in particular for transmitting the operating data, the network access device being data-connectable to an external data processing system, the data processing system being data-connectable to at least one context parameter sensor unit at least indirectly detecting the operation of the handheld metering device and/or detecting environmental operating conditions of the handheld metering device and generating context parameter data therefrom, the metering system, in particular the data processing system, having a comparison unit configured at least to compare operating data of the operating data unit with target operating data and/or to compare context parameter data of the context parameter unit with target context parameter data and to generate a comparison result, in particular a deviation of the data from the target data identified in the course of the comparison.

Furthermore, the invention relates to a method for operating an electronic laboratory metering system for liquids, the system comprising at least one electronic handheld metering device having at least one operation sensor unit detecting the operation of the handheld metering device and generating corresponding operating data and, in particular, storing said operating data in a storage device of the handheld metering device, the handheld metering device having an interface module by means of which the handheld metering device is connected to an external network access device via a data connection, in particular for transmitting the operating data, the network access device being data-connectable to an external data processing system, the data processing system being data-connectable to at least one context parameter sensor unit at least indirectly detecting the operation of the handheld metering device and/or detecting environmental operating conditions of the handheld metering device and generating context parameter data therefrom, the metering system, in particular the data processing system, having a comparison unit at least comparing operating data of the operation sensor unit with target operating data and/or comparing context parameter data of the context parameter sensor unit with target context parameter data and generating a comparison result, in particular a deviation of the data from the target data identified in the course of the comparison.

Laboratory metering systems and methods for operating said systems are known from the state of the art. EP 0 999 432 B1, for example, discloses a method for operating an electronic metering system and a metering system in which data can be transferred via an interface between a handheld metering device and a data processing system, the data ensuring that routines for operating the handheld metering device can be defined on the data processing system or an input interface assigned to the data processing system and that the data can be transmitted to the handheld metering device and can be stored by the handheld metering device. Said fact allows for a simple operation or programming of the handheld metering device for preparing and performing complex work routines. Additionally, such a system and the corresponding method allow for a certain amount of instruction of an operator during the operation or when corresponding work routines are performed.

Furthermore, EP 3 141 909 A1 discloses a laboratory metering system for liquids in which a visual comparison is realized by means of a camera and an output is conveyed to or displayed for an operator based on the visual comparison, wherein said output is to indicate possible errors or inaccuracies when work routines are performed. Thereby, compliance with the defined routines can thus be generally improved while the work routines are being performed or errors by an operator can be indicated more easily while the handheld metering device is being operated.

The state of the art also discloses system and methods which allow for a recording of the performed work routines by means of corresponding operating data of the handheld metering device and/or by means of context parameter sensor units at least indirectly detecting the operation of the handheld metering device and/or detecting environmental operating conditions when the systems and methods are being used for operating an electronic laboratory metering system.

However, the disadvantage of the state of the art is that the known methods and systems meet the requirements of a quality management of the samples and/or liquids produced by means of the system in an insufficient manner or do not meet said requirements. Only an extremely limited tracing of the samples or liquids can be realized for the produced or provided liquids by the system or by the method. This means that, in particular ex post, the correct and complete performance or processing of the respective work routine for producing the sample or the liquid cannot be traced or can only be traced in a rudimentary manner.

SUMMARY OF THE INVENTION

Starting from the aforementioned state of the art, the object of the invention is to indicate an electronic laboratory metering system for liquids which allows for an autonomous or automatic validation of performed or processed work routines and therefore improves the traceability of produced liquids and also facilitates and improves the quality management for laboratories and similar institutions.

Furthermore, the object is to indicate a method which allows for an improved quality management in laboratories and similar institutions.

Concerning the system, said object is attained by the features; i.e., a generic system is provided with a documentation unit which is configured to generate and to store protocol data sets relating to the operation of the at least one handheld metering device, in particular comprising at least the operating data and/or the context parameter data, the documentation unit being connected to the comparison unit in such a manner that the comparison results of the comparison unit can be transmitted to the documentation unit and the documentation unit is configured to store the comparison results as part of the protocol data sets, in particular in a manner assigned to the corresponding operating data and/or context parameter data, in particular to add to said comparison results after an operation of the handheld metering device has ended.

Concerning the method, said object is attained by the features disclosed herein.

Advantageous embodiments of the invention are disclosed in the dependent claims. All combinations of at least two features disclosed in the description, the claims and/or the figures constitute part of the scope of the invention.

The idea of the invention is to detect and record data as comprehensive and as conclusive as possible in the course of the operation of the handheld metering device, i.e., during work routines of any kind, including routines for calibrating the handheld metering device, the detection and recording of data being realized by the operation sensor unit and the context parameter sensor unit, additional specifications or target data being generated and provided in addition to the mere recording of data relating to the operation and the environmental operating conditions, said specifications or target data describing an optimum operation or a correct handling and correct environment conditions; additionally, the idea of the invention is to ultimately realize a comparison of the operating data and the context parameter data with the corresponding target data in the course of the operation of the handheld metering device or following the operation of the handheld metering device and to record and store the comparison result at least following the operation of the handheld metering device together with the other recorded values and data relating to the operation in the form of extended protocol data sets.

This allows for the realization of an analysis which is independent from the time between the operation of the handheld metering device and a corresponding processing of a work routine; additionally, it can be assessed whether all recorded operating data and/or context parameter data meet the target requirements or are within the range of the target requirements within the scope of the processing of the work routine for exactly one sample or for exactly one liquid. In other words, the protocol data sets generated and stored by the documentation unit contribute to the automatic validation or to the self-validation of the performed work routines, because the protocol data sets themselves show if there is a deviation from the target requirements or target data and especially to which work step or to which context parameter or the like said deviation relates. In a particularly advantageous manner, this allows for an objective and useful comparability of different samples or liquids which are generated or created by means of supposedly identical work routines, because a comparability can only be assumed if comparison results of the comparisons drawn by the comparison unit of the protocol data sets generated and stored by the documentation unit do not show any (significant) deviations. Conversely, this means that if the comparisons of at least one protocol data set of a sample or liquid shows such a deviation, the comparability with another sample or liquid supposedly generated by means of an identical work routine is nonexistent in the first place or can be excluded. This facilitates the work in laboratories or similar institutions in a previously unknown manner, because, in particular, a quantitative and qualitative comparability or the exclusion of a corresponding comparability between different samples or liquids created or generated by means of supposedly identical work routines is made possible.

The handheld metering device of the present system can be a metering device which operates according to the air cushion principle and which has an integrated piston-cylinder unit. Alternatively, the handheld metering device can be realized as a micro metering device which has a micro diaphragm pump and/or a free jet metering apparatus. Alternatively, the handheld metering device can be a dispenser which operates according to the positive displacement principle and whose cylinder and piston can be realized as consumable goods, in particular as disposable devices. The handheld metering device can also be realized as a multichannel metering device. The network access device of the system according to the invention can be realized as a so-called gateway, for example, which data-communicates with the handheld metering device in a bidirectional manner. Standardized connection technologies or connection protocols, such as Bluetooth or WLAN, can be used for the data connection. However, the data connection between the network access device and the handheld metering device can also be realized or established in a wired manner or via physical contact means. In said embodiment, the network access device and the handheld metering device can have contact means, such as plugs or the like, which are realized in a complementary manner. For example, the network access device can be realized in such a manner that said device is configured to receive and output data in the form of a network protocol and has corresponding outputs and inputs for data. For example, the network access device can be connected to the data processing system via a Local Area Network connection (LAN connection).

The data processing system itself can be realized as a server-client system. PCs, tablets, smartphones or other portable electronic devices are used as clients. Alternatively, the client or clients can be realized as augmented reality devices and can be configured to generate image content, in particular virtual image content, and to overlay said content with real image content and to generate and output a representation of the overlaid virtual and real image content. The client or clients can comprise the essential data infrastructure, in particular software. Alternatively, the server can comprise the essential data infrastructure, in particular the software, and the client or clients serve only to access the server infrastructure.

Accordingly, the comparison unit and/or the documentation unit are assigned to a server of a data processing system or to one or several clients of the data processing system; i.e., the server or the client(s) comprise the comparison unit and/or the documentation unit. The data connection between the data processing system and the handheld metering device via the intermediary network access device and the context parameter sensor unit allows for an essentially free transmission of the operating data of the operation sensor unit, the context parameter data of the context parameter sensor unit and the corresponding target operating data and target context parameter data between the individual elements of the system. It is thus possible that both the data processing system and the handheld metering device itself have a comparison unit. Furthermore, it is thus possible to provide the comparison results of a comparison unit, independently of the disposition or assignment of the comparison unit, to the other system components or elements of the system, in particular to the documentation unit, but also to other system components.

The operation sensor unit can have one or a plurality of sensors which detect the direct operation of the handheld metering device. For example, a sensor can be provided which detects the operation of the piston-cylinder unit of the handheld metering device. Additionally or alternatively, a sensor can be provided which detects the operation of an electrical drive device for the piston-cylinder unit. Furthermore, a motion sensor or inertial sensor can be provided which detects the translation and/or rotation and/or acceleration of the handheld metering device. However, the operation sensor unit can also be configured to detect static operating data. For example, the operation sensor unit detects or identifies a serial number or another identification means of the handheld metering device. Other sensors of the operation sensor unit can be realized as an operating hours counter, in particular an operating hours counter depending on a calibration date of the handheld metering device, or as a camera for the optical detection of the operation of the handheld metering device inside or outside the handheld metering device or the like.

According to a first advantageous embodiment of the metering system, said metering system can comprise at least one output unit, in particular comprised by the handheld metering device, for outputting user instructions and/or user information, the output unit being connected to the comparison unit in such a manner that comparison results, in particular a deviation of the data from the target data identified in the course of the comparison, are directly outputted. Such output units can be used for a variety of applications. For example, other user instructions or user information can be outputted via the output unit, said other user instructions or user information allowing for or improving a guiding of the operator or user in the course of the processing of a work routine. This means that the output unit can be configured to output user instructions which facilitate or allow the compliance with the target operating data and/or target context parameter data. The present embodiment also provides that the output unit is connected to the comparison unit, which means that comparison results, in particular the deviation of the data from the target data, can be outputted to an operator or user. This requires, however, that the system directly receives as many operating and/or context parameter data as possible and the corresponding target data directly or that said data are transmitted to the comparison unit and a direct evaluation, i.e., a direct comparison, is realized, in particular if only one single, central comparison unit is provided. However, this could require a permanent data transmission between the handheld metering device and the other elements of the system. In order to realize the data connection between the handheld metering device and the other system components in an efficient manner, in particular in an energy-efficient manner with respect to the energy consumption of the handheld metering device, an alternative embodiment provides an additional comparison unit which is assigned to the handheld metering device and which allows for an energy efficient internal data communication between the operation sensor unit and a storage device comprising target operating data, for example, a comparison result thus being prepared at least for the operating data in the course of the operation of the handheld metering device; on the basis of said comparison result, outputs can be generated by means of the output unit without the need for an external communication of the handheld metering device via the network access device and the other system components connected thereto. Advantageously, the comparison results of a comparison unit generated by the handheld metering device are transmitted to the network access device in intervals or after the operation of the handheld metering device has ended, in particular after a work routine has ended, and are made accessible to a documentation unit accordingly. In other words, this means that, for example, a spatial distribution of the comparison unit over the individual system components may be useful, as long as it is ensured that the respective comparison results generated by the comparison units and stored are collected and the respective data are combined into protocol data sets at least after the operation of the handheld metering device has ended or after a work routine has been performed by means of the handheld metering device.

According to another particularly preferred embodiment of the metering system, the at least one context parameter sensor unit is configured to detect static and/or dynamic context parameters. For example, the context parameter sensor unit can be configured to detect dynamic context parameters, for example a room temperature in the laboratory or room in which the handheld metering device is used. Alternatively, the context parameter sensor unit can detect static context parameters. For example, the context parameter sensor unit can be configured to detect a user identity and thus detect the static identity of a user of the handheld metering device, the identity being static at least for the realization of one work routine. To this end, the context parameter sensor unit can have an input interface, for example, by means of which a user identifies himself/herself via corresponding inputs, for example via an alias and a password. In a particularly advantageous manner in this context, the system can comprise means which allow for the loading or retrieving of user-specific system settings after an identification of a user in the system or at a handheld metering device. A particularly preferred embodiment provides means by means of which user-specific settings or parameters for a handheld metering device are retrieved and/or are transmitted to the handheld metering device. Additionally, a plurality of other static and/or dynamic context parameters can be detected by the at least one context parameter senor unit. Air pressure and other meteorological data can be such context parameters, for example.

According to another particularly preferred embodiment of the system, the system comprises at least one classification unit which is or can at least be connected to the context parameter sensor unit and which is additionally configured to classify the detected operation of the handheld metering device and/or the detected environmental operating conditions, wherein a context parameter can be derived from the classification and/or context parameter data can be generated by means of the classification. On the one hand, the classification unit can thus be used to translate dynamic context parameters or context parameter data into static or quasi-static context parameters and context parameter data. On the other hand, the classification unit can be used to translate an environmental operating condition which is not amenable to a comparison with target data otherwise into a classified context parameter and thus to make said environmental operating condition amenable to the comparison of a comparison unit. For example, user classes can be assigned and stored in the classification unit for a number of registered users, an assignment of the user to a defined user class thus being realizable by means of the context parameter sensor unit in the course of the detection of an identified user and the respective user class of the user who is currently registered at a handheld metering device thus being comparable to a target user class by the comparison unit. Additional information and data with respect to the production of liquids or the treatment of samples, in particular non-numerical context parameters, which are not amenable to a comparison otherwise, are made amenable to the comparison of a comparison unit and the value of the resulting protocol data sets can be increased accordingly. In principle, a classification unit can also be connected to the operation sensor unit and can be configured to classify operating data. For example, a classification of movements or accelerations of the handheld metering device detected by means of a corresponding sensor can be classified by means of a classification unit which is realized accordingly and said classification can be made amenable to a comparison by means of the comparison unit.

According to another particularly preferred embodiment, the system comprises a documentation storage device which is configured to store and/or to catalog protocol data sets. This allows for conclusive protocol data sets which significantly improve and facilitate the quality management according to the invention and ensure a qualitative and quantitative comparability of samples and liquids—subsequently, where appropriate—, in particular over a long period of time. Furthermore, the cataloging of the protocol data sets by means of the documentation storage device provides particular advantages for the system. For example, the protocol data sets can be made accessible by a search query, in particular by the data processing system. Furthermore, the cataloging allows the protocol data sets to be searched with respect to their content by means of the documentation storage device.

Another particularly advantageous embodiment of the system provides a conversion device which is configured to convert protocol data sets into a data format of an electronic laboratory journal or to embed the protocol data sets into laboratory information management systems. This ensures that the protocol data sets are made available to a documentation and/or auditing system which is as comprehensive as possible; in a particularly advantageous manner, precisely those comparison results included in the protocol data sets are of particularly high value for the higher-level systems, in particular for a laboratory information management system, because said comparison results allow for a very wide-ranging and clear assessment about the quality of the respective samples or liquids. Accordingly, an ever-increasing demand for auditability of known metering systems can be obtained by providing the conversion device.

In an advantageous embodiment of the invention, the system can also comprise an evaluation unit, wherein the evaluation unit is particularly preferably connected to the documentation storage device and is configured to evaluate protocol data sets and/or to compare protocol data sets and can output results from the evaluation via an output interface, in particular for further processing by the metering system. Advantageously, this makes the protocol data sets amenable to a subsequent evaluation and a subsequent comparison and a corresponding output to an operator or user. This means, for example, that a user can use the evaluation unit before further analysis steps of produced samples or liquids are carried out or after further analysis activities and the user can carry out an evaluation with respect to the quality of the respective sample or liquid or compare the qualities of different samples based on the corresponding output of an output interface. In this way, it can be established, for example, whether, because of their previous treatment, in particular within the scope of the metering system according to the invention, different samples or liquids can be compared to one another at all or can be used as a common basis for qualitative or quantitative evaluation purposes. The evaluation unit can be realized in a highly automated manner, the evaluation and/or the comparison of protocol data sets thus taking place without significant support by an operator or a user. However, the evaluation unit can also be realized in such a manner that it is influenced or controlled by a user or operator. In a particularly advantageous manner, this allows for the limitation or weighting of the evaluation and/or the comparison with respect to specific parts of the protocol data sets or to specific data of the protocol data sets.

According to an another particularly preferred embodiment of the metering system, a programming unit can be provided, the programming unit preferably being comprised by the data processing system and being configured to define work routines and/or to define device parameters of a parameter unit of the handheld metering device, the programming unit being configured to generate and to store target operating data and/or target context parameter data based on defined work routines and/or device parameters. Advantageously, the programming unit can basically realize that the operator or user of the system, in particular the operator or the user of the handheld metering device, can create work routines which are tailored to his purposes and that he/she can transmit data relating to the work routines to the handheld metering device, if required, said realization thus allowing for a simple programming of the handheld metering device, in particular if the programming unit is comprised by the external data processing system, and allowing for a particularly flexible use of the handheld metering device. In addition to work routines, the programming unit can also be configured to define device parameters of a parameter unit of the handheld metering device. This means, for example, that calibration data for the handheld metering device or other device parameters, such as control parameters for an electric drive unit or other data, are defined by the programming unit and are transmitted or transferred to the handheld metering device, if required, and are stored there once more, if required. In the broadest sense, remote control or, more precisely, remote setting of the handheld metering device can thus be realized.

However, according to the preferred embodiment, the programming unit can also be configured to generate and to store target operating data and/or target context parameter based on defined work routines and/or device parameters. This means that, if it is established within the scope of a definition of a work routine, for example, that a specific step is to be realized at a specific time or that a specific work routine is to be realized exclusively in a specific range of a room temperature, the programming unit is configured to generate and to store target data based on said or similar specifications; during or, in particular, after the performance of the work routine, said target data can be compared to the detected operating data and/or context parameter data by the comparison unit and can be added to the protocol data sets via the documentation unit. The same can be applied to the definition of device parameters. For example, the programming unit can be configured to enable the operation of the handheld metering device for liquids which have different properties, in particular different densities and different viscosities, by generating and storing different sets of device parameters by the programming unit and transmitting them to the handheld metering device for the use of a handheld metering device for a corresponding liquid. Additionally, within the scope of such a definition of device parameters for the definition of liquids or liquid classes, for example, target data, in particular target operating data, can be generated automatically, or at least semi-automatically, by a confirmation in the course of a user interaction, for example. Said target data, too, can be transmitted to the comparison unit together with the operating data during or after an operation of the system, in particular an operation of the handheld metering device, and the comparison results can be assigned to the protocol data sets by means of the documentation unit.

Furthermore, the programming unit can generally be suitable for the output of a list of available work routines and/or device parameters or device parameter sets via an output interface which is connected to the programming unit. As already mentioned, the programming unit can support or cause the transmission of corresponding data relating to work routines and/or device parameters to one or several handheld metering devices. Additionally, the programming unit can allow for an exchange of defined work routines and/or device parameters or device parameter sets with other metering systems or other data processing systems.

According to another particularly preferred embodiment of the metering system, the network access device is comprised by a fastening device for the detachable fastening of at least one handheld metering device. For example, the fastening device can be realized as a stand which has corresponding reception and/or fastening means for the detachable fastening of the handheld metering device. Preferably, the stand can be configured to receive and/or fasten more than one handheld metering device. Additionally, the fastening device can have corresponding contact means in order to establish a wired data connection to handheld metering devices which are disposed in the reception and/or fastening means, for example.

According to an alternative advantageous embodiment, the network access device can be realized as a separate system component and can be installed in an independent or free manner. This is particularly advantageous if a standardized protocol, such as WLAN, is used for the communication, i.e., for the data connection to the handheld metering device. For example, the network access device can be used as a system component of the system according to the invention and, at the same time, for other functions and activities in this case. Conversely, this means that existing network access devices can be integrated into the system according to the invention, if applicable. In this way, additional functionalities of the system can be realized, in particular via a further-reaching and improved connectivity, and the system setup and maintenance costs can be reduced simultaneously. Accordingly, the network access device can preferably be realized as a WLAN hub or WLAN router.

Different advantages can be achieved by the combination or integration of the network access device with or into the fastening device. Said fastening devices are normally used near the place of work and/or operation of the handheld metering device, a relatively short transmission path thus having to be bridged for the, in particular wireless, data connection between the network access device and at least one handheld metering device. Furthermore, the fastening devices can have means for charging electrical energy storages of a handheld metering device which is received and fastened in the fastening device; to this end, energy transmission means must be provided for the wired transmission of energy or for the inductive transmission of energy, for example. In this case, the energy transmission means can be used to establish or provide the data connection to the handheld metering device, if required.

According to another particularly preferred embodiment of the metering system, the context parameter sensor unit is configured to duplicate or detect a measured value or an output signal of a laboratory liquid measuring device. A pH measuring device, a volume measuring device, a density measuring device, a filling level measuring device or a mass measuring device, such as a balance, can be used as said liquid measuring device. In a particularly advantageous manner, the indirect operation of the handheld metering device and therefore the use of the metering system can be documented in a precise and conclusive manner by duplicating or detecting a measured value or an output signal of such a measuring device. Accordingly, a very extensive process control can be realized and a very extensive quality management can be realized by means of the system according to the invention if corresponding target context parameter data on the detected or duplicated measured values or output signals are provided or defined in the course of the comparison by means of the comparison unit and the comparison results are subsequently assigned to the protocol data sets by the documentation unit. The property and the development of the samples or liquids can be detected and evaluated beyond the direct operation of the handheld metering device by capturing or detecting the measured values or output signals of the measuring device or measuring devices; as a result, conclusive protocol data sets can be obtained if the corresponding data are combined with the obtained or obtainable comparison results and the correct and/or complete performance of work routines and/or calibration processes can be assessed in a highly meaningful manner. Additionally, the analysis with respect to the comparability or the equivalence of different samples or liquids or of samples or liquids which are produced according to supposedly identical work routines, but which are produced according to different approaches or work routines performed at different times can thus be improved. For example, the context parameter sensor unit can be configured to duplicate or detect a measured value of a pH measuring device which detects the pH of a sample or liquid in the course of the use of the metering system and of the handheld metering device and said measured value can be compared with corresponding target context parameter data by the comparison unit during or after the operation of the handheld metering device, the comparison results being assigned to the other data and information of the protocol data sets by the documentation unit and being stored together with the protocol data sets.

The system can particularly preferably comprise an automated handling device for moving and operating the handheld metering device. The handling device can have electrical, pneumatic and/or hydraulic positioning and/or drive units. The handling device is preferably realized as a robotic device, in particular as a robot arm.

Furthermore, the invention relates to a method for operating an electronic laboratory metering system for liquids, the system comprising at least one electronic handheld metering device having at least one operation sensor unit detecting the operation of the handheld metering device and generating corresponding operating data and, in particular, storing said operating data in a storage device of the handheld metering device, the handheld metering device having an interface module by means of which the handheld metering device is connected to an external network access device via a data connection, in particular for transmitting the operating data, the network access device being data-connectable to an external data processing system, the data processing system being data-connectable to at least one context parameter sensor unit at least indirectly detecting the operation of the handheld metering device and/or detecting environmental operating conditions of the handheld metering device, the metering system, in particular the data processing system, having a comparison unit comparing at least operating data of the operation sensor unit with target operating data and/or comparing context parameter data of the context parameter unit with target context parameter data and generating a comparison result, in particular a deviation of the data from the target data identified in the course of the comparison, and the method according to the invention being characterized in that the metering system comprises a documentation unit which generates and stores protocol data sets relating to the operation of the at least one handheld metering device, in particular comprising at least the operating data and/or the context parameter data, the documentation unit being connected to the comparison unit in such a manner that the comparison results of the comparison unit are transmitted to the documentation unit and the documentation unit stores the comparison results as part of the protocol data sets, in particular in a manner assigned to the corresponding operating data and/or context parameter data, in particular adds to said comparison results after an operation of the handheld metering device has ended.

In a particularly advantageous manner, the method according to the invention allows for a traceability as extensive as possible of the performed activities, in particular of the performed work routines, subsequent to an operation of a corresponding handheld metering device or subsequent to the respective operation of the metering system in order to ultimately allow conclusions to be drawn for a certain sample or a certain liquid regarding its proper processing or treatment and therefore regarding its comparability with other samples and liquids. In an embodiment according to the invention, this ensures that the method allows for a particularly high level of quality management for the metering system.

The abovementioned advantageous effects of the system according to the invention—to which reference is made at this point—are realized by the method according to the invention. Reference is also made to the abovementioned description, at least with respect to the advantageous effects, for the realizations and advantageous embodiments of the method to be described below if corresponding embodiments of the system have been described above.

According to a first such advantageous embodiment of the method, the output of user instructions and/or user information can be realized by means of at least one output unit, in particular comprised by the handheld metering device, the output unit being connected to the comparison unit in such a manner that comparison results, in particular a deviation of the data from the target data identified in the course of the comparison, are directly outputted. As described above, it can be beneficial for this purpose to transmit the operating data and the context parameter data to a comparison unit while the handheld metering device is still in operation. Alternatively, the comparison unit can be split or several comparison units can be provided, at least one or a part of which is disposed in the handheld metering device, a comparison being realizable at least for the operating data without data communication with the remaining system components while the handheld metering device is still in operation. Preferably, the comparison data, in particular the comparison results, can initially be stored locally in the handheld metering device and can be made available to the other system components via the network access device merely in intervals or periodically, in particular only after the operation of the handheld metering device has ended.

The advantage of the corresponding output of user information or user instructions is that a deviation from the target data is directly detected and communicated to the user; the corresponding operation of the handheld metering device, in particular the performance of a work routine, can thus be cancelled and restarted, if required. Even if this is not the case, the documentation unit provided according to the invention and the linking of operating data, context parameter data and the corresponding results from the comparison of the data with the target data allow—at least subsequently, i.e., after the use of the handheld metering device or of the metering system has ended—an assessment and a determination without any time limit as to whether the work routine has been performed correctly or within the scope of given tolerances and, accordingly, whether the generated or produced sample or liquid has reached a target state and whether said sample or liquid can be compared to other properly produced samples and liquids with respect to quality and quantity.

Another particularly preferred embodiment of the method provides the detection of static and/or dynamic context parameters via at least one context parameter sensor unit. An ambient temperature or a user and/or operator identity can be detected, for example.

Likewise, the method can preferably entail that a classification of the detected operation of the handheld metering device and/or the detected environmental operating conditions is carried out by means of at least one classification unit which is connected to the context parameter sensor unit, wherein a context parameter can be derived from the classification and/or context parameter data can be generated by means of the classification. As indicated above, this can be advantageous for the method whenever a detected context parameter or an environmental operating condition is not initially suitable for a comparison with a target specification. For example, the classification can be used for the classification of a detected user and for the comparison with a defined user class or for the comparison with a target user class.

Furthermore, according to an advantageous embodiment of the method, protocol data sets can be stored and/or cataloged by means of a documentation storage device. In this way, the protocol data sets can be located, searched, searched or located on the basis of specified criteria and further processed or prepared, if required, at any later point in time after their generation.

According to another particularly preferred embodiment of the method, a conversion of protocol data sets into a data format of an electronic laboratory journal or the embedding into laboratory information management systems can be realized by means of a conversion device. The advantageous effects of the protocol data sets, in particular the comparison results linked to the recorded data by the documentation unit, can thus be used or made usable beyond the metering system.

Another embodiment of the method provides the evaluation of protocol data sets and/or the comparison of protocol data sets by means of an evaluation unit which is connected to a documentation storage device, an output of the results from the evaluation, in particular for further processing by the metering system, being realized via an output interface of the metering system. In this way, individual samples or liquids can be examined and/or compared, subsequent to their production and/or processing, with respect to the question whether the target requirements have been met and whether an analysis of the samples and liquids can be assumed to be conclusive and different samples or liquids can be assumed to be comparable.

According to another embodiment of the method, work routines and/or device parameters of a parameter unit of the handheld metering device are defined by means of a programming unit, in particular comprised by the data processing system, the programming unit generating and/or storing target operating data and/or target context parameter data based on defined work routines or device parameters. It is thus possible to use the metering system for a great variety of applications, because flexible work routines can be preprogrammed and can be transmitted to the handheld metering device, if required. At the same time, the realization of the comparison of context parameter data and operating data with corresponding target data is facilitated, because the programming of the work routines and/or of the device parameters automatically, or at least semi-automatically, leads to the definition or specification of target operating data and/or target context parameter data; said target operating data and/or target context parameter data can then be compared to the detected operating data and context parameter data and the comparison result can be stored. The programming unit can be realized in such a manner that new work routines can be generated and/or work routines can be changed. Additionally, the programming unit can be realized in such a manner that generated or changed work routines are subjected to an automatic examination and/or validation.

Advantageously, the work routines and/or device parameters generated or changed by means of the programming unit and sets of device parameters can be stored and organized in a corresponding storage device. Additionally, data which are required for performing a work routine and the device parameters which are required, for example, for a use of the handheld metering device with different liquid classes can be transmitted from the programming unit to the handheld metering device, in particular a corresponding storage device of the handheld metering device, via the corresponding data connections and can be retrieved or used by a control unit of the handheld metering device.

Another alternative embodiment of the method provides the duplication or the detection of a measured value or an output signal of a laboratory liquid measuring device by means of at least one context parameter sensor unit. The laboratory environment of the metering system can thus be optimally integrated into the quality management created by the metering system. In particular, context parameters which at least indirectly result from the operation of the metering system or which are connected to the operation of the metering system can also be used for the long-term, extensive and conclusive documentation of the performed work routines within the scope of a corresponding comparison and a storage of the comparison results and can provide particularly conclusive information on the validity or the correct production of the samples and liquids, an automatic linking to the protocol data sets, in particular, adding particular value, because the protocol data sets at large are or can be clearly assigned to a sample or liquid.

BRIEF DESCRIPTION OF THE DRAWINGS

Advantageous embodiments and variants of the invention are apparent from the following description of preferred exemplary embodiments and from the drawings.

In the drawings.

DETAILED DESCRIPTION

Figure 1:
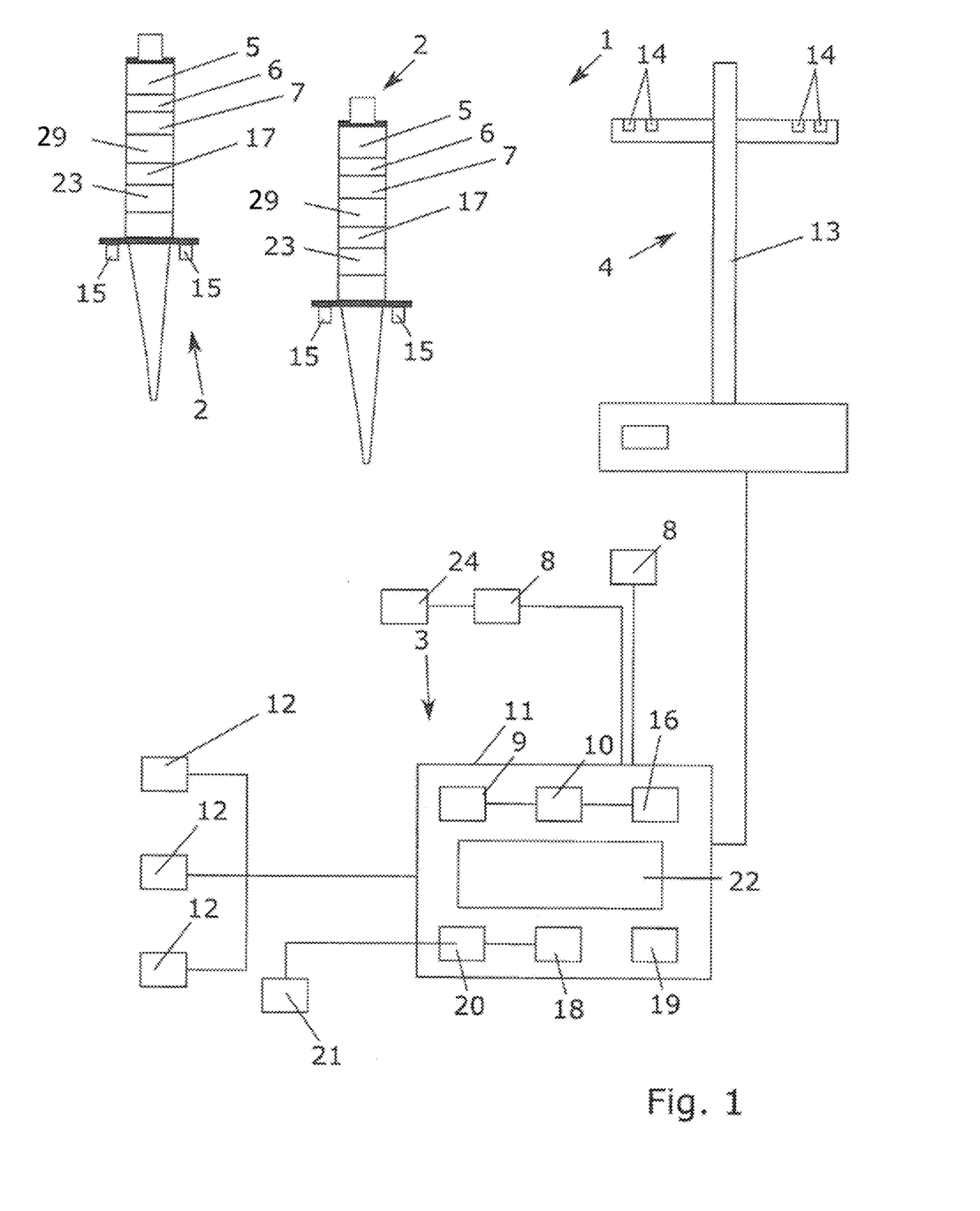
FIG. 1 is a schematic view of a metering system according to the invention.

FIG. 1 shows a metering system 1 which has a plurality of handheld metering devices 2, a data processing system 3 and a network access device 4. Handheld metering devices 2 each comprise an operation sensor unit 5 which detects the operation of handheld metering devices 2 and generates corresponding operating data and stores said operating data in a storage device 6 of handheld metering devices 2.

Additionally, handheld metering devices 2 each comprise an interface module 7 by means of which handheld metering devices 2 can be connected to network access device 4 via a data connection, in particular for transmitting operating data, network access device 4 being data-connectable to data processing system 3, and data processing system 3 being data-connectable to at least one context parameter sensor unit 8 at least indirectly detecting the operation of handheld metering devices 2 and/or detecting environmental operating conditions of handheld metering devices 2 and generating context parameter data therefrom, metering system 1, in particular data processing system 3, having a comparison unit 9 configured at least to compare operating data of operation sensor unit 5 with target operating data and/or to compare context parameter data of context parameter sensor unit 8 with target context parameter data and to generate a comparison result, in particular a deviation of the data from the target data identified in the course of the comparison.

Furthermore, metering system 1, for example data processing system 3 of metering system 1, comprises a documentation unit 10 which is configured to generate and to store protocol data sets relating to the operation of at least one handheld metering device 2, in particular comprising at least the operating data and/or the context parameter data, documentation unit 10 being connected to comparison unit 9 in such a manner that the comparison results of comparison unit 9 can be transmitted to documentation unit 10 and documentation unit 10 is configured to store the comparison results as part of the protocol data sets, in particular in a manner assigned to the corresponding operating data and/or context parameter data, in particular to add to said comparison results after an operation of handheld metering devices 2 has ended.

In the example of FIG. 1, data processing system 3 is realized as a server-client system which comprises a server 11 and a plurality of clients 12 which are also data-connected to one another. In the example of the illustration of FIG. 1, server 11 comprises comparison unit 9 and documentation unit 10. For example, clients 12 can be realized as mobile electronic devices, such as tablets or the like. Clients 12 can allow for a corresponding access to server 11, in particular via one or several graphical user interfaces.

For example, network access device 4 can be realized as a fastening device 13 for the detachable fastening of at least one handheld metering device 2. The data connection or the communication between handheld metering devices 2 and network access device 4 can be realized via WLAN or Bluetooth, for example. Alternatively, network access device 4 can have contact means 14 which are realized in a complementary manner to contact means 15 of handheld metering devices 2, allowing a wired connection to be established between handheld metering devices 2 and network access device 4 in addition or as an alternative to a wireless connection. The connection can be used to transmit energy to an energy storage (not shown in FIG. 1) of handheld metering devices 2. Additionally, the connection established via contact means 14, 15 can be used for the data connection between network access device 4 and handheld metering devices 2.

In exemplary metering system 1, data processing system 3, in particular server 11, can have a classification unit 16 which is connected to context parameter sensor unit 8 and which is configured to classify the detected operation of handheld metering device 2 and/or the detected environmental operating conditions, wherein a context parameter can be derived from the classification and/or context parameter data can be generated by means of the classification. For example, a user can be identified via context parameter sensor unit 8 and can be assigned to a user class via classification unit 16.

Handheld metering devices 2 of metering system 1 can also comprise an output unit 17 for outputting user instructions and/or user information, output unit 17 being connected to comparison unit 29 in such a manner that comparison results, in particular a deviation of the data from the target data identified in the course of the comparison, are directly outputted. As described above, handheld metering devices 2 can have a comparison unit 29 themselves in order to avoid or to reduce energy-intensive communication between handheld metering devices 2 and network access device 4, said comparison unit 29 comparing at least the operating data detected by operation sensor 5 with target operating data and outputting a deviation as the comparison result via output unit 17, if applicable.

Additionally, data processing system 3 can have a documentation storage device 18 which is configured to store and/or to catalog protocol data sets. Data processing system 3, in particular server 11, can also comprise a conversion device 19 which is configured to convert protocol data sets into a data format of an electronic laboratory journal or to embed the protocol data sets into a laboratory information management system. Furthermore, metering system 1 according to the embodiment of the illustration of FIG. 1 can comprise an evaluation unit 20 which is connected to documentation storage device 18 and which is configured to evaluate protocol data sets and/or to compare protocol data sets and which can output results from the evaluation via an output interface 21, in particular for further processing by the metering system. Additionally, data processing system 3, in particular server 11, can comprise a programming unit 22 which is configured to define work routines and/or to define device parameters of a parameter unit 23 of handheld metering device 2, programming unit 22 being configured to generate and to store target operating data and/or target context parameter data based on defined work routines and/or device parameters.

In the example of the illustration of FIG. 1, metering system 1 comprises a second context parameter sensor unit 8 which is configured to duplicate or to detect a measured value or an output signal of a laboratory liquid measuring device 24.

In addition to said components, the metering system can have a plurality of other advantageous components, of which just a few representative components are to be described below.

Metering system 1, in particular the handheld metering devices and the data processing system, can have means and devices for the reliable localization of handheld metering device 2. Additionally, data processing system 3 can have means and devices which allow for a reservation or a booking of handheld metering devices 2. Users can preferably reserve handheld metering devices 2 for use via clients 12 and the corresponding access to server 11. Furthermore, data processing system 3 can process the detected operating data and/or the context parameter data by means of other devices of the metering system. For example, the operating data can be stored and processed by data processing system 3 in such a manner that a maintenance and/or administration unit detects a current state of handheld metering devices 2 and predicts a future state, in particular future signs of wear and/or fatigue, of handheld metering devices 2, if applicable.

Metering system 1 can also comprise additional units, in particular comprised by data processing system 3, which use the abovementioned registered and classified or categorized users and the corresponding data. For example, a functionality of clients 12 which is tiered on the basis of user classes can be provided, said tiered functionality being reflected in a use depending on user classes or in access rights to programming unit 22, evaluation unit 20 and/or documentation storage device 18 depending on user classes.

For example, operating data sensor unit 5 of handheld metering devices 2 can detect stroke movements of a piston unit of handheld metering device 2 or the state of a drive unit of handheld metering device 2. Alternatively or additionally, operation sensor unit 5 can detect the movement and accelerations of handheld metering device 2 itself. Context parameter sensor units 8 can detect different environmental conditions which can be relevant within the scope of the use of metering system 1. These environmental conditions include liquid properties of the processed liquid, environmental parameters and the like.

As indicated above, access to programming unit 22 can be granted via clients 12 in order to generate and/or to change work routines or device parameters. After a corresponding generation or change of the work routines or device parameters, they can be transmitted to one or several handheld metering devices 2 depending on an authorization class of a user, if applicable. Target data can be generated and stored automatically or semi-automatically together with the generation or change of work routines or device parameters by the data processing system, in particular by server 11, particularly preferably by programming unit 22. In the course of the method, said target data can be compared to the detected operating data and context parameter data and the comparison result can be stored together with the operating data and context parameter data in documentation unit 10. However, the target data can also be defined and stored in another manner, in particular by manual specification by the user via clients 12, for example.

In order to establish wireless communication between handheld metering devices 2 and network access device 4, a transmission according to a standard, such as Bluetooth or WLAN, can be realized. JSON-RPC or MQTT can be used as an interface protocol, for example. In a particularly preferred manner, it is guaranteed that interface modules 7 of handheld metering devices 2 allow for a secure login and authentication in a wireless network of metering device 1.

Figure 2:
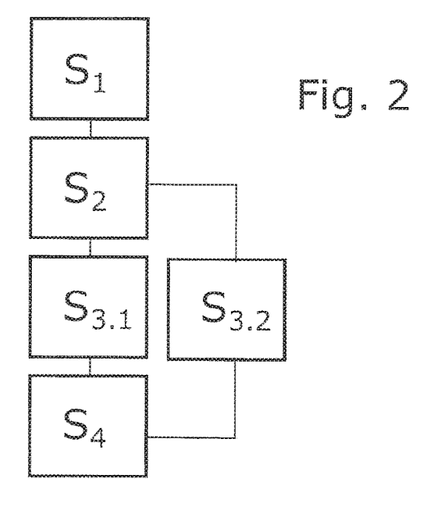
FIG. 2 is a schematic view of a process of a method according to the invention.

In FIG. 2, an exemplary method for operating an electronic laboratory metering system is shown. For example, the method can start with a user selecting a liquid or liquid class and determining a work routine to be performed at handheld metering device 2 in a first method step $S_1$. The liquid or liquid class can be defined by device parameters which are stored in parameter unit 23 and which were transmitted from programming unit 22 to handheld metering device 2 in advance, if applicable. The data relating to a workflow to be performed or a work routine to be performed can be stored by a storage device of the handheld metering device and can also have been defined by means of programming unit 22 and transmitted to a storage device of handheld metering device 2 prior to method step $S_1$. The selection of the liquid or liquid class and the selection of the work routine in step $S_1$ can already be subject to authorization or access control, said control—possibly with the help of data processing system 3—checking, for example, whether a user currently registered for or logged in at handheld metering device 2 has a corresponding authorization or authorization class for handling a liquid or liquid class, whether the logged-in or registered user has a sufficient competence or training class for performing the selected workflow or for performing the selected work routine, whether the handheld metering device to be used has a calibration, currentness of the calibration and/or device class which corresponds to the work routine or which is required for the performance of the work routine.

In a subsequent method step $S_2$, the user starts to perform the respective activities, in particular to process a work routine using handheld metering device 2. Instructions and information which facilitate compliance with and/or adherence to the work routine can be outputted via an output unit 17. Furthermore, operation sensor unit 5 and context parameter sensor units 8 can detect and store operating data and can detect and store context parameter data during step $S_2$. In the example of FIG. 2, the method is to be realized in such a manner that, at first, the operating data and context parameter data are only collected or detected during method step $S_2$. After completion of method step $S_2$, an additional method step $S_{3.1}$ follows in which the detected operating data and context parameter data are supplied to a documentation unit 10 via the respective data connections and are stored in protocol data sets or in one protocol data set. In a method step $S_{3.2}$ which runs in parallel with method step $S_{3.1}$ in the example of FIG. 2, but which can also take place before or after method step $S_{3.1}$, the operating data and the context parameter data are supplied or made available to a comparison unit 9. In addition to the operating data and context parameter data, comparison unit 9 is also supplied with target operating data and target context parameter data in method step $S_{3.2}$.

Additionally, a comparison between the data and the target data is realized in method step $S_{3.2}$, wherein comparison results are obtained which reflect, in particular, a deviation between the data and the target data. In a subsequent method step $S_4$, the comparison results obtained in method step $S_{3.2}$ are assigned to the protocol data sets generated in method step $S_{3.1}$.

REFERENCE SIGNS 1 metering system
2 handheld metering device
3 data processing system
4 network access device
5 operation sensor unit
6 storage device
7 interface module
8 context parameter sensor unit
9 comparison unit
10 documentation unit
11 server
12 client
13 fastening device
14 contact means
15 contact means
16 classification unit
17 output unit
18 documentation storage device
19 conversion device
20 evaluation unit
21 output interface
22 programming unit
23 parameter unit
24 liquid measuring device
$S_1$ method step
$S_2$ method step
$S_{3.1}$, $S_{3.2}$ method step
$S_4$ method step

The invention claimed is:

1. An electronic laboratory metering system (1) for liquids, comprising:
at least one electrical handheld metering device (2) having at least one operation sensor unit (5) detecting the operation of the handheld metering device (2) and generating corresponding operating data and, the handheld metering device (2) having an interface module (7) by means of which the handheld metering device (2) can be connected to an external network access device (4) via a data connection, the network access device (4) being data-connectable to an external data processing system (3), the data processing system (3) being data-connectable to at least one context parameter sensor unit (8) (a) at least indirectly detecting the operation of the handheld metering device (2) and/or (b) detecting environmental operating conditions of the handheld metering device (2), and generating context parameter data therefrom, the data processing system (3) having a comparison unit (9, 29) configured at least (a) to compare operating data of the operation sensor unit (5) with target operating data and/or (b) to compare context parameter data of the at least one context parameter sensor unit (8) with target context parameter data, and to generate a comparison result,
wherein
the metering system (1) comprises a documentation unit (10) which is configured to generate and to store protocol data sets relating to the operation of the at least one handheld metering device (2), the documentation unit (10) being connected to the comparison unit (9, 29) in such a manner that the comparison results of the comparison unit (9, 29) can be transmitted to the documentation unit (10) and the documentation unit (10) is configured to store the comparison results as part of the protocol data sets.

2. The metering system according to claim 1, wherein the handheld metering device (2) further comprises at least one output unit (17) for outputting user instructions and/or user information, the output unit (17) being connected to the comparison unit (9, 29) in such a manner that comparison results, comprising a deviation of the data from the target data identified in the course of the comparison, are directly outputted.

3. The metering system according to claim 1, wherein the at least one context parameter sensor unit (8) is configured to detect static and/or dynamic context parameters.

4. The metering system according to claim 1, wherein the at least one context parameter sensor unit (8) is connected to a classification unit (16) of the data processing system (3), wherein the classification unit (16) is configured to classify the detected operation of the handheld metering device (2) and/or the detected environmental operating conditions, wherein a context parameter can be derived from the classification and/or context parameter data can be generated by means of the classification.

5. The metering system according to claim 1, wherein the data processing system (3) further comprises a documentation storage device (18) which is configured to store and/or to catalog protocol data sets.

6. The metering system according to claim 5, wherein the data processing system (3) further comprises at least one evaluation unit (20) which is connected to the documentation storage device (18) and which is configured to evaluate protocol data sets and/or to compare protocol data sets and which can output results from the evaluation via an output interface (21), for further processing by the metering system.

7. The metering system according to claim 1, wherein the data processing system (3) further comprises a conversion device (19) which is configured to convert the protocol data sets into a data format of an electronic laboratory journal or to embed the protocol data sets into laboratory information management systems.

8. The metering system according to claim 1, wherein the data processing system (3) further comprises a programming unit (22) for defining work routines and/or for defining device parameters of a parameter unit (23) of the handheld metering device (2), the programming unit (22) being configured to generate and to store target operating data and/or target context parameter data based on defined work routines and/or device parameters.

9. The metering system according to claim 1, wherein the network access device (4) further comprises a fastening device (13) for the detachable fastening of at least one handheld metering device (2).

10. The metering system according to claim 1, wherein the context parameter sensor unit (8) is configured to duplicate or to detect a measured value or an output signal of a laboratory liquid measuring device (24).

11. The metering system according to claim 1, wherein the operation sensor unit (5) stores said operating data in a storage device (6) of the handheld metering device (2), wherein the handheld metering device (2) can be connected to the external network access device (4) for transmitting the operating data, wherein the data processing system (3) has the comparison unit (9), wherein the comparison result is a deviation of the data from the target data identified in the course of the comparison, wherein the protocol data sets comprise at least the operating data and/or the context parameter data, and wherein the documentation unit (10) is configured to store the comparison results as part of the protocol data sets in a manner assigned to the corresponding operating data and/or context parameter data to add to said comparison results after an operation of the handheld metering device (2) has ended.

* * * * *